(12) United States Patent
Uhr et al.

(10) Patent No.: US 6,197,799 B1
(45) Date of Patent: Mar. 6, 2001

(54) DITHIAZOLDIOXIDES AND THE USE THEREOF AS MICROBICIDES

(75) Inventors: Hermann Uhr, Krefeld; Klaus Stenzel, Düsseldorf; Martin Kugler, Leichlingen; Heinrich Schrage, Krefeld, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/077,648

(22) PCT Filed: Nov. 25, 1996

(86) PCT No.: PCT/EP96/01587
§ 371 Date: Jun. 2, 1998
§ 102(e) Date: Jun. 2, 1998

(87) PCT Pub. No.: WO97/20830
PCT Pub. Date: Jun. 12, 1997

(30) Foreign Application Priority Data

Dec. 7, 1995 (DE) .............................................. 195 45 635

(51) Int. Cl.$^7$ ............................. A01N 43/82; C07D 285/01
(52) U.S. Cl. ............................................... 514/360; 548/123
(58) Field of Search .............................. 548/123; 514/360

(56) References Cited

U.S. PATENT DOCUMENTS

| | | |
|---|---|---|
| 3,345,374 | 10/1967 | Dickoré et al. . |
| 4,017,638 | 4/1977 | Dittrich et al. . |
| 4,271,306 | 6/1981 | Aoyagi . |
| 4,962,102 | 10/1990 | Beck et al. . |

FOREIGN PATENT DOCUMENTS 2608488    9/1976    (DE) .

*Primary Examiner*—Patricia L. Morris
(74) *Attorney, Agent, or Firm*—Norris McLaughlin & Marcus

(57) ABSTRACT

The invention relates to novel dithiazole dioxides, to processes for their preparation and to their use in crop protection and in the protection of materials.

8 Claims, No Drawings

DITHIAZOLDIOXIDES AND THE USE THEREOF AS MICROBICIDES

The invention relates to novel dithiazole dioxides, to processes for their preparation and to their use in crop protection and in the protection of materials.

Dithiazoles are already described, a biological activity has not been mentioned.

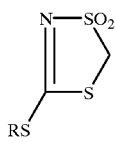

(see K. Dickoré, Lieb. Ann. Chem. 671, 135 (1964); U.S. Pat No. 3,345,374).

Surprisingly, it has now been found that the novel compounds of the general formula (I)

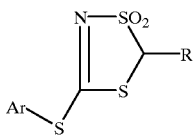

(I)

in which
R represents hydrogen or optionally substituted alkyl, alkenyl or alkinyl and
Ar represents optionally substituted aryl
are outstandingly suitable for protecting crops and materials.

The formula (I) provides a general definition of the compounds according to the invention. Preference is given to compounds of the formula (I) in which R represents hydrogen, straight-chain or branched alkyl having 1 is 10 carbon atoms, straight-chain or branched alkenyl having 2 to 10 carbon atoms or straight-chain or branched alkinyl having 2 to 10 carbon atoms, which is optionally mono- to polysubstituted by identical or different substituents from the group consisting of halogen, alkoxy having 1 to 6 carbon atoms, halogenoalkoxy having 1 to 6 carbon atoms and 1 to 9 identical or different halogen atoms, alkylthio having 1 to 6 carbon atoms, halogenoalkylthio having 1 to 6 carbon atoms and 1 to 9 identical or different halogen atoms, acyl having 1 to 6 carbon atoms, acyloxy having 1 to 6 carbon atoms, (alkoxy)-carbonyl having 1 to 6 carbon atoms, amino, which is optionally substituted by identical or different substituents from the group consisting of alkyl and aryl, optionally substituted phenoxy, aryl, pyridyl or pyridyloxy, nitro or cyano, and Ar represents aryl,
which is optionally mono- to pentasubstituted by halogen, alkyl having 1 to 10 carbon atoms, halogenoalkyl having 1 to 8 carbon atoms and 1 to 8 identical or different halogen atoms, alkoxy having 1 to 10 carbon atoms, halogenoalkoxy having 1 to 8 carbon atoms and 1 to 8 identical or different halogen atoms, alkylthio having 1 to 10 carbon atoms, halogenoalkylthio having 1 to 8 carbon atoms and 1 to 8 identical or different halogen atoms, amino, monoalkylamino having straight-chain or branched alkyl radicals having 1 to 6 carbon atoms, dialkylamino having identical or different, straight-chain or branched alkyl radicals having in each case 1 to 6 carbon atoms, cycloalkyl having 1 to 6 carbon atoms, methylenedioxy, difluoromethylenedioxy, chlorofluoromethylenedioxy, dichloromethylenedioxy, nitro or cyano.

Particular preference is given to compounds of the formula (I) in which

R represents hydrogen, straight-chain or branched alkyl having 1 to 8 carbon atoms, straight-chain or branched alkenyl having 2 to 8 carbon atoms or straight-chain or branched alkinyl having 2 to 8 carbon atoms, which is optionally mono- to tetrasubstituted by identical or different substitutents from the group consisting of fluorine, chlorine, alkoxy having 1 to 5 carbon atoms, halogenoalkoxy having 1 to 5 carbon atoms and 1 to 5 fluorine and/or chlorine atoms, alylthio having 1 to 5 carbon atoms, halogenoalkylthio having 1 to 5 carbon atoms and 1 to 5 fluorine and/or chlorine atoms, acyl having 1 to 5 carbon atoms, acyloxy having 1 to 5 carbon atoms, alkoxycarbonyl having 1 to 5 carbon atoms, amino which is optionally substituted by identical or different substituents from the group consisting of alkyl having 1 to 4 carbon atoms and phenyl, optionally substituted phenoxy, aryl, pyridyl, pyridyloxy, nitro or cyano, and Ar represents phenyl which is optionally mono- to tetrasubstituted by fluorine, chlorine, alkyl having 1 to 8 carbon atoms, halogenoalkyl having 1 to 6 carbon atoms and 1 to 6 fluorine and/or chlorine atoms, alkoxy having 1 to 8 carbon atoms, halogenoalkoxy having 1 to 6 carbon atoms and 1 to 6 fluorine and/or chlorine atoms, alkylthio having 1 to 8 carbon atoms, halogenoalkylthio having 1 to 6 carbon atoms and 1 to 6 fluorine and/or chlorine atoms, amino, monoalkylamino having alkyl radicals of 1 to 4 carbon atoms, dialkylamino having identical or different alkyl radicals having in each case 1 to 4 carbon atoms, cycloalkyl having 1 to 6 carbon atoms, methylenedioxy, difluoromethylenedioxy, chlorofluoromethylenedioxy, dichloromethylenedioxy, nitro or cyano.

Very particularly preferably, R represents hydrogen, methyl, ethyl, n- and i-propyl, n-, s-, i- and t-butyl, allyl and propargyl which are optionally substituted by fluorine and/or chlorine, methoxy or methylthio, and Ar represents phenyl which is optionally mono- to trisubstituted by fluorine, chlorine, methyl, ethyl, n- and i-propyl, n-, s-, i- and t-butyl, methoxy, ethoxy, trifluoromethyl, trifluoromethoxy, cyano and/or phenoxy.

Furthermore, it has been found that the compounds of the formula (I) are obtained when the salts of the general formula (II)

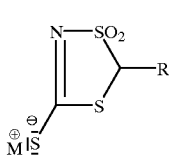

(II)

in which
R is as defined above and
M$^\oplus$ represents an alkali metal or alkaline earth metal ion, in particular Na$^+$, K$^+$
are reacted with diazonium salts of the general formula (III)

 (III)

in which
Ar is as defined above and
A$^\ominus$ represents the anion of a mineral acid, in aqueous/alkaline solution, if appropriate in the presence of a catalyst.

Preferably, a solution of (II) is mixed with a base and, if appropriate, with a catalyst, and then with the diazonium salt solution (III). Preferred bases are alkali metal hydroxides such as, for example, potassium hydroxide or sodium hydroxide. Suitable catalysts are all catalysts which promote the exchange of the diazonium function against sulphur-containing radicals.

Preference is given to using Cu(I) salts or copper powder. During the addition of the diazonium salt solution, the temperature may be varied within a wide range. In general, the reaction is carried out between −30° C. and +60° C., preferably between −20° C. and +40° C. The preparation of the diazonium salt solution from anilines is carried out by methods known from the literature.

The salts of the general formula (II) can also be prepared by methods known from the literature (see references on p. 1). Either salts of the formula (II) which have been isolated in solid form, or solutions prepared in situ may be used.

The active compounds according to the invention have strong microbicidal action and can be employed for controlling unwanted microorganisms, such as fungi and bacteria, in crop protection and in the protection of materials.

In the present context, the term industrial materials refers to non-living materials which have been prepared for use in industry. Examples are industrial materials which are to be protected by the active compounds according to the invention against microbial alteration or destruction, adhesives, sizes, paper and card, textiles, leather, wood, coating compositions and plastics articles, cooling lubricants and other materials which can be infested or decomposed by microorganisms. In the context of the materials to be protected mention may also be made of parts of production plants, for example cooling water circuits, which may be adversely affected by reproduction of microorganisms. Preferred industrial materials in the context of the present invention are adhesives, sizes, papers and cards, leather, wood, coating compositions, cooling lubricants and heat transfer fluids.

Examples of microorganisms which can bring about degradation or an alteration in the industrial materials are bacteria, fungi, yeasts, algae and slime organisms. The active compounds or compositions according to the invention preferably act against bacteria, fungi, especially mould fungi, and also against slime organisms and algae.

By way of example, mention may be made of microorganisms of the following genera:

Alternaria, such as *Alternaria tenuis,*
Aspergillus, such as *Aspergillus niger,*
Chaetomium, such as *Chaetomium globosum,*
Coniophora, such as *Coniophora puteana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Scierophoma, such as *Sclerophoma pityophila,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

Fungicidal compositions in crop protection are employed for controlling Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*
Phytophthora species, such as, for example, Phytophthora infestans;
Pseudoperonospora species, such as, for example, *Pseudoperonospora humuli* or *Pseudoperonospora cubense;*
Plasmopara species, such as, for example, *Plasmopara viticola;*
Peronospora species, such as, for example, Peronospora pisi or *Peronospora brassicae;*
Erysiphe species, such as, for example, *Erysiphe graminis,*
Sphaaerotheca species, such as, for example, *Sphaerotheca fuliginea;*
Podosphaera species, such as, for example, *podosphaera leucotricha;*
Venturia species, such as, for example, *Venturia inaequalis;*
Pyrenophora species, such as, for example, *Pyrenophora teres* or *Pyrenophora graminea* (conidia form: Drechslera, syn: Helminthosporium);
Cochliobolus species, such as, for example, *Cochluobolus sativus* (conidia form: Drechslera, syn: Helminthosporium);
Uromyces species, such as, for example, *Uromyces appendiculatus;*
Puccinia species, such as, for example, *Puccinia recondita;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;*
Pseudocercosporella species, such as, for example, *Pseudocercosporella herpotrichoides.*

The good crop safety of the active compounds also permits a treatment of plants at the concentrations required for controlling plant diseases, a treatment of above-ground parts of plants, of vegetative propagation stock and seed and of the soil being possible.

Depending on their respective physical and/or chemical properties, the active compounds of the formula (I) can be converted into customary formulations, such as solutions, emulsions, suspensions, powders, foams, pastes, granules, aerosols and very fine capsules in polymeric substances.

These formulations and compositions are prepared in a known manner, for example by mixing the active compounds with extenders, that is, liquid solvents, liquefied gases under pressure, and/or solid carriers, if appropriate with the use of surfactants, that is emulsifiers and/or dispersants and/or foam-formers. If the extender used is water, it is also possible to use for example organic solvents as auxiliary solvents. Essentially, suitable liquid solvents are: aromatics, such as xylene, toluene and alkylnaphthalenes, chlorinated aromatics or chlorinated aliphatic hydrocarbons, such as chlorobenzenes, chloroethylene or methylene chloride, aliphatic hydrocarbons, such as cyclohexane or paraffins, for example mineral oil fractions, alcohols, such as butanol or glycol and their ethers and esters, ketones, such as acetone, methyl ethyl ketone, methyl isobutyl ketone or cyclohexanone, strongly polar solvents, such as dimethyl formamide or dimethyl sulphoxide, and water; by liquefied gaseous extenders or carriers are meant liquids which are gaseous at ambient temperature and under atmospheric pressure, for example aerosol propellants, such as halogenated hydrocarbons and butane, propane, nitrogen and carbon dioxide; suitable solid carriers are: for example ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and synthetic granules of organic and inorganic meals, and granules of organic material such as sawdust, coconut shells, maize hobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates: suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Possible further additives are mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanin dyestuffs, and trace nutrients such as salts of iron, manganese, boron, copper, cobalt, molybdenum and zinc.

The efficacy and the activity spectrum of the active compounds of the formula (I) and of the compositions preparable therefrom, of precursors and of formulations in general can be increased by adding, if appropriate, further antimicrobial compounds, fungicides, bactericides, herbicides, insecticides or other active compounds, so as to widen the spectrum of activity or to obtain particular effects such as, for example, additional protection against insects. These mixtures may have a wider activity spectrum than the compounds according to the invention.

In many cases, synergistic effects are obtained, i.e. the activity of the mixture is greater than the activity of the individual components. Particularly suitable co-components are, for example, the following compounds:

Triazoles such as:

Amitrole, azocyclotin, BAS 480F, bitertanol, difenoconazole, fenbuconazole, fenchlorazole, fenethanil, fluquinconazole, flusilazole, flutriafol, imibenconazole, isozofos, myclobutanil, metconazole, epoxyconazole, paclobutrazol, penconazole, propioconazole, (±)-cis-1-(4-chlorophenyl)-2-(1H-1,2,4-triazol-1-yl)-cycloheptanol, tetraconazole, triadimefon, triadimenol, triapenthenol, triflumizole, triticonazole, uniconazole and their metal salts and acid adducts.

Imidazoles such as:

Imazalil, pefurazoate, prochloraz, triflumizole, 2-(1-tert-butyl)-1-(2-chlorophenyl)-3-(1,2,4-triazol-1-yl)-propan-2-ol, thiazolecarboxanilides such as 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one, and their metal salts and acid adducts.

Methyl(E)-2-[2-[6-(2-cyanophenoxy)pyrimidin-4-yloxy]phenyl]-3-methoxyacrylate, methyl(E)-2-[2-[6-(2-thioamidophenoxy)pyrimidin-4-yloxy]phenyl]-3-methoxyacrylate, methyl(E)-2-[2-[6-(2-fluorophenoxy)pyrimidin-4-yloxy ]phenyl]-3-methoxyacrylate, methyl(E)-2-[2- [6-(2,6-difluorophenoxy)pyrimidin-4-yloxy]phenyl]-3-methoxyacryl ate, methyl(E)-2-[2-[3-(pyrimidin-2-yloxy)phenoxy]phenyl]-3-methoxyacrylate, methyl(E)-2-[2-[3-(5-methylpyrimidin-2-yloxy)-phenoxy]phenyl]-3-methoxyacrylate, methyl(E)-2-[2-[3-(phenyl-sulphonyloxy)phenoxy]phenyl-3-methoxyacrylate, methyl(E)-2-[2-[3-(4-nitrophenoxy)phenoxy]phenyl]-3-methoxyacrylate, methyl (E)-2-[2-phenoxyphenyl]-3-methoxyacrylate, methyl(E)-2-[-2-(3,5-dimethylbenzoyl)pyrrol-1-yl]-3-methoxyacrylate, methyl(E)-2-[2-(3-methoxyphenoxy)phenyl]-3-methoxyacrylate, methyl(E)-2[-2-(2-phenylethen-1-yl)-phenyl]-3-methoxyacrylate, methyl(E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl(E)-2-(2-[3-(alpha-hydroxybenzyl)phenoxyl]phenyl)-3-methoxyacrylate, methyl(E)-2-(2-(4-phenoxypyridin-2-yloxy)phenyl)-3-methoxyacrylate, methyl(E)-2-[2-(3-n-propyloxyphenoxy)phenyl]3-methoxyacrylate, methyl(E)-2-[2-(3-isopropyloxyphenoxy)phenyl]-3-methoxyacrylate, methyl(E)-2-[2-[3-(2-fluorophenoxy)phenoxy]phenyl]-3-methoxyacrylate, methyl(E)-2-[2-(3-ethoxyphenoxy)phenyl]-3-methoxyacrylate, methyl(E)-2-[2-(4-tert-butylpyridin-2-yloxy)phenyl]-3-methoxyacrylate, methyl(E)-2-[2-[3-(3-cyanophenoxy)phenoxy]phenyl]-3-methoxyacrylate, methyl(E)-2-[2-[(3-methylpyridin-2-yloxymethyl)phenyl]-3-methoxyacrylate, methyl(E)-2-[2-[6-(2-methylphenoxy)pyrimidin-4-yloxy]phenyl]-3-methoxyacrylate, methyl(E)-2-[2-(5-bromopyridin-2-yloxymethyl)phenyl]-3-methoxyacrylate, methyl(E)-2-[2-(3-(3-iodopyridin-2-yloxy)phenoxy)phenyl]-3-methoxyacrylate, methyl(E)-2-[2-[6-(2-chloropyridin-3-yloxy)pyrimidin-4-yloxy]phenyl]-3-methoxyacrylate, (E),(E)methyl-2-[2-(5,6-dimethylpyrazin-2-ylmethoximinomethyl)phenyl]-3-methoxyacrylate, (E)-methyl-2-{2-[6-(6-methylpyridin-2-yloxy)pyrimidin-4-yloxy]phenyl}-3-methoxyacrylate, (E),(E)methyl-2-{2-(3-methoxyphenyl)methyloximinomethyl]phenyl}-3-methoxyacrylate, (E)methyl-2-{2-(6-(2-azidophenoxy)-pyrimidin-4-yloxy]phenyl}-3-methoxyacrylate, (E),(E)methyl-2-{2-[6-phenylpyrimidin-4-yl)-methyloximinomethyl]phenyl}-3-methoxyacrylate, (E),(E)methyl-2-{2-[(4-chlorophenyl)-methyloximinomethyl]phenyl}-3-methoxyacrylate, (E)methyl-2-{2-[6-(2-n-propylphenoxy)-1,3,5-triazin-4-yloxy]phenyl}-3-methoxyacrylate, (E),(E)methyl-2-{2-[(3-nitrophenyl)methyloximinomethyl]phenyl}-3-methoxyacrylate;

Succinate dehydrogenase inhibitors such as:
  Fenfuram, furcarbanil, cyclafluramid, furmecyclox, seedvax, metsulfovax, pyrocarbolid, oxycarboxin, shirlan, mebenil (mepronil), benodanil, flutolanil (Moncut);

Naphthalene derivatives such as terbinafine, naftifine, butenafine, 3-chloro-7-(2-aza-2,7,7-trimethyl-oct-3-en-5-ine);

Sulfenamides, such as dichlofluanid, tolylfluanid, folpet, fluorfolpet; captan, captofol;

Benzimidazoles, such as carbendazim, benomyl, furathiocarb, fuberidazole, thiophonatmethyl, thiabendazole or their salts;

Morpholine derivatives, such as tridemorph, fenpropimorph, falimorph, dimethomorph, dodemorph, aldimorph, fenpropidine and their arylsulphonates, such as, for example, p-toluenesulphonic acid and p-dodecylphenylsulphonic acid;

Dithiocarbamates, cufraneb, ferbam, mancopper, mancozeb, maneb, metam, metiram, thiram zeneb, ziram;

Benzothiazoles, such as 2-mercaptobenzothiazole;

Benzamides, such as 2,6-dichloro-N-(4-trifluoromethylbenzyl)-benzamide;

Boron compounds, such as boric acid, boric esters, borax;

Formaldehyde and formaldehyde-releasing compounds, such as benzyl alcohol mono(poly)-hemiformal, oxazolidine, hexa-hydro-S-triazines, N-methylolchloroacetamide, paraformadehyde, nitropyrin, oxolinic acid, tecloftalam;

Tris-N-(cyclohexyldiazeneiumdioxy)-aluminium, N-(cyclohexyldiazeneiumdioxy)-tributyltin or K salts, bis-N-(cyclohexyldiazeniumdioxy)-copper;

N-methylisothiazolin-3-one, 5-chloro-N-methylisothiazolin-3-one, 4,5-dichloro-N-octylisothiazolin-3-one, N-octyl-isothiazolin-3-one, 4,5-trimethylene-isothiazolinone, 4,5-benzoisothiazolinone, N-methylolchloroacetamide;

Aldehydes, such as cinnamaldehyde, formaldehyde, glutardialdehyde, β-bromocinnamaldehyde;

thiocyanates, such as thiocyanatomethylthiobenzothiazole, methylenebisthiocyanate, and the like;

Quaternary ammonium compounds, such as benzyldimethyltetradecylammonium chloride, benzyldimethyldodecylammonium chloride, didecyldimethaylammonium chloride;

Iodine derivatives, such as diiodomethyl p-tolyl sulphone, 3-iodo-2-propinyl alcohol, 4-chloro-phenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate;

Phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol and their alkali metal and alkaline earth metal salts;

Microbicides having an activated halogen group, such as chloroacetamide, bronopol, bronidox, tectamer, such as 2-bromo-2-nitro-1,3-propanediol, 2-bromo-4'-hydroxy-acetophenone, 2,2-dibromo-3-nitrile-propionamide, 1,2-dibromo-2,4-dicyanobutane, β-bromo-β-nitrostyrene;

Pyridines, such as 1-hydroxy-2-pyridinethione (and their Na, Fe, Mn, Zn salts), tetrachloro-4-methylsulphonylpyridine, pyrimethanol, mepanipyrim, dipyrithion 1-hydroxy-4-methyl-6-(2,4,4-trimethylpentyl)-2(1H)-pyridine;

Metal soaps, such as tin naphtenate, copper naphtenate, zinc naphtenate, tin octoate, copper octoate, zinc octoate, tin 2-ethylhexanoate, copper 2-ethylhexanoate, zinc 2-ethylhexanoate, tin oleate, copper oleate, zinc oleate, tin phosphate, copper phosphate, zinc phosphate, tin benzoate, copper benzoate and zinc benzoate;

Metal salts, such as copper hydroxycarbonate, sodium dichromate, potassium dichromate, potassium chromate, copper sulphate, copper chloride, copper borate, zinc fluorosilicate, copper fluorosilicate;

Oxides, such as tributyltin oxide, $Cu_2O$, CuO, ZnO;

Dialkyldithiocarbamates, such as Na and Zn salts of dialkyldithiocarbamates, tetramethylthiuram disulphide, potassium N-methyl-dithiocarbamate;

Nitriles, such as 2,4,5,6-tetrachloroisophthalonitrile, disodium cyanodithioimidocarbamate;

Quinolines, such as 8-hydroxyquinoline, and their Cu salts;

Mucochloric acid, 5-hydroxy-2(5H)-furanone;

4,5-Dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, potassium N-hydroxymethyl-N'-methyl-dithiocarbamate, 2-oxo-2-(4-hydroxy-phenyl)acethydroximic acid chloride; phenyl 2-chloro-cyano-vinyl sulphone;

phenyl 1,2-dichloro-2-cyano-vinyl sulphone:

Ag, Zn or Cu-containing zeolites, alone or enclosed in polymeric active compounds.

Very particularly preferred mixtures are those with
  azaconazole, bromuconazole, cyproconazole, dichlobutrazol, diniconazole, hexaconazole, metaconazole, penconazole, propiconazole, tebuconazole, methyl (E)-methoximino[α-(o-tolyloxy)-o-tolyl)]acetate, methyl (E)-2-{2-[6-(2-cyanophenoxy)-pyrimidin-4-yl-oxy]phenyl}-3-methoxyacrylate, methfuroxam, carboxin, fenpiclonil, 4-(2,2-difluoro-1,3-benzodioxol-4-yl)-1H-pyrrole-3-carbonitrile, butenafine, imazalil, N-methyl-isothiazolin-3-one, 5-chloro-N-methylisothiazolin-3-one, N-octylisothiazolin-3-one, benzisothiazolinones, N-(2-hydroxypropyl)-amino-methanol, benzyl alcohol (hemi)-formal, glutaraldehyde, omadine, dimethyl dicarbonate, and/or 3-iodo-2-propinyl n-butylcarbamate.

Furthermore, highly active mixtures are also prepared with the following active ingredients:

Fungicides:
  acypetacs, 2-aminobutane, ampropylfos, anilazine, benalaxyl, bupirimate, quinomethionate, chloroneb, chlozolinate, cymoxanil, dazomet, diclomezine, dichloram, diethofencarb, dimethirimol, diocab, dithianon, dodine, drazoxolon, edifenphos, ethirimol, etridiazole, fenarimol, fenitropan, fentin acetate, fentin hydroxide, ferimzone, fluazinam, fluromide, flusulfamide, flutriafol, fosetyl, fthalide, furalaxyl, guazatine, hymexazol, iprobenfos, iprodione, isoprothiolane, metalaxyl, methasulfocarb, nitrothalisopropyl, nuarimol, ofurace, oxadiyl, perflurazoate, pencycuron, phosdiphen, pimaricin, piperalin, procymidone, propamocarb, propineb, pyrazophos, pyrifenox, pyroquilone, quintozene, tar oils, tecnazene, thicyofen, thiophanate-methyl, tolclofos-methyl, triazoxide, trichlamide, tricyclazole, triforine, vinclozolin.

Insecticides:

phosphoric esters such as azinphos-ethyl, azinphos-methyl, α-1(4-chlorophenyl)-4-(O-ethyl, S-propyl)-phosphoryloxy-pyrazole, chlorpyrifos, coumaphos, demeton, demeton-S-methyl, diazinon, dichlorvos, dimethoate, ethoate, ethoprophos, etrimfos, fenitrothion, fenthion, heptenophas, parathion, parathion-methyl, phosalone, phoxim, pirimiphos-ethyl, pirimiphos-methyl, profenofos, prothiofos, sulfprofos, triazophos and trichlorphon;

Carbamates such as aldicarb, bendiocarb, α-2-(1-methylpropyl)-phenylmethylcarbamate, butocarboxim, butoxycarboxim, carbaryl, carbofuran, carbosulfan, cloethocarb, isoprocarb, methomyl, oxamyl, pirimicarb, promecarb, propoxur and thiodicarb;

Organosilicon compounds, preferably dimethyl(phenyl) silyl-methyl 3-phenoxybenzyl ethers such as dimethyl-(4-ethoxyphenyl)-silylmethyl 3-phenoxybenzyl ether or (dimethylphenyl)-silyl-methyl-2-phenoxy-6-pyridyl methyl ethers such as, for example, dimethyl-(9-ethoxy-phenyl)-silylmethyl-2-phenoxy-6-pyridyl methyl ether or [(phenyl)-3-(3-phenoxyphenyl)-propyl](dimethyl)-silanes such as, for example, (4-ethoxyphenyl)-[3-(4-fluoro-3-phenoxyphenyl-propyl]dimethyl-silane, silafluofen;

Pyrethroids such as allethrin, alphamethrin, bioresmethrin, byfenthrin, cycloprothrin, cyfluthrin, decamethrin, cyhalothrin, cypermethrin, deltamethrin, alpha-cyano-3-phenyl-2-methylbenzyl 2,2-dimethyl-3-(2-chloro-2-trifluoro-methylvinyl) cyclopropanecarboxylate, fenpropathrin, fenfluthrin, fenvalerate, flucythrinate, flumethrin, fluvalinate, permethrin, resmethrin and tralomethrin;

Nitroimines and nitromethylenes such as 1-[(6-chloro-3-pyridinyl)-methyl]-4,5-dihydro-N-nitro-1H-imidazole-2-amine (imidacloprid), N-[(6-chloro-3-pyridyl)methyl-]N²-cyano-N¹-methylacetamide (NI-25);

abamectin, AC 303, 630, acephate, acrinathrin, alanycarb, aldoxycarb, aldrin, amitraz, azamethiphos, Bacillus thuringiensis, phosmet, phosphamidon, phosphine, prallethrin, propaphos, propetamphos, prothoate, pyraclofos, pyrethrins, pyridaben, pyridafenthion, pyriproxyfen, quinalphos, RH-7988, rotenone, sodium fluoride, sodium hexafluorosilicate, sulfotep, sulfuryl fluoride, tar oils, teflubenzuron, tefluthrin, temephos, terbufos, tetrachlorvinphos, tetramethrin, O-2-tert.-butyl-pyrimidin-5-yl-o-isopropyl-phosphorothiate, thiocyclam, thiofanox, thiometon, tralomethrin, triflumuron, trimethacarb, vamidothion, Verticillium Lacanii, XMC, xylylcarb, benfuracarb, bensultap, bifenthrin, bioallethrin, MERbioallethrin (S)-cyclopentenyl isomer, bromophos, bromophos-ethyl, buprofezin, cadusafos, calcium polysulfide, carbophenothion, cartap, quinomethionate, chlordane, chlorfenvinphos, chlorfluazuron, chlormephos, chlorpicrin, chlorpyrifos, cyanophos, beta-cyfluthrin, alpha-cypermethrin, cyophenothrin, cyromazine, dazomet, DDT, demeton-S-methylsulphon, diafenthiuron, dialifos, dicrotophos, diflubenzuron, dinoseb, deoxabenzofos, diazacarb, disulfoton, DNOC, empenthrin, endosulfan, EPN, esfenvalerate, ethiofencarb, ethion, etofenprox, fenobucarb, fenoxycarb, fensulfothion, fipronil, flucycloxuron, flufenprox, flufenoxuron, fonofos, formetanate, formothion, fosmethilan, furathiocarb, heptachlor, hexaflumuron, hydramethylnon, hydrogen cyanide, hydroprene, IPSP, isazofos, isofenphos, isoprothiolane, isoxathion, iodfenphos, kadethrin, lindane, malathion, mecarbam, mephosfolan, mercurous, chloride, metam, Metarthizium, anisopliae, methacrifos, methamidophos, methidathion, methiocarb, methoprene, methoxychlor, methyl isothiocyanate, metholcarb, mevinphos, monocrotophos, naled, Neodiprion sertifer NPV, nicotine, omethoate, oxydemeton-methyl, pentachlorophenol, petroleum oils, phenothrin, phenthoate, phorate;

Molluscicides:

fentin acetate, metaldehyde, methiocarb. niclosamide, thiodicarb, trimethacarb.

Algicides:

copper sulphate, dichlororphen, endothal, fentin acetate, quinoclamine.

Herbicides:

acetochlor, acifluorfen, aclonifen, acrolein, alachlor, alloxydim, ametryn, amidosulfuron, amitrole, ammonium sulfamate, anilofos, asulam atrazine, aziptrotryne, benazolin, benfluralin, benfuresate, bensulfuron, bensulfide, bentazone, benzofencap, benzthiazuron, bifenox, bilanafos, borax, dichlorprop, dichlorprop-P, diclofop, diethatyl, difenoxuron, difenzoquat, diflufenican, dimefuron, dimepiperate, dimethachlor, dimethametryn, dimethipin, dimethylarsinic acid, dinitramine, dinoseb, dinoseb, dinoseb acetate, dinoseb, bromacil, bromobutide, bromofenoxim, bromoxynil, butachlor, butamifos, fuenachlor, butralin, butylate, carbetamide, CGA 184927, chlormethoxyfen, chloramben, chlorbromuron, chlorbutam, chlorfurenol, chloridazon, chlorimuron, chlornitrofen, chioroacetic acid, achloropicrin, chlorotoluron, chloroxuron, chlorprepham, chlorsulfuron, chlorthal, chlorthiamid, cinmethylin, cinofulsuron, clethodim, clomazone, clomeprop, clopyralid, cyanamide, cyanazine, dinoseb acetate, dinoterb, diphenamid, dipropetryn, diquat, dithiopyr, diduron, DNOC, PPX-A 788, DPX-E96361, DSMA, eglinazine, endothal, EPTC, esprocarb, ethalfluralin, ethidimuron, ethofumesate, fenoxaprop, fenoxaprop-P, fenuron, flamprop, flamprop-M, flazasulfuron, fluazifop, fluazifop-P, fluchloralin, flumeturon, fluorocgycofen, fluoronitrofen, flupropanate, flurenol, fluridone, flurochloridone, fluoroxypyr, cycloate, cycloxydim, 2,4-D, daimuron, dalapon, dazomet, 2,4-DB, desmedipham, desmetryn, dicamba, dichlorbenil, isoproturon, isouron, isoxaben, isoxapyrifop, lactofen, lenacil, linuron, LS830556, MCPA, MCPA-thioethyl, MCPB, mecoprop, mecoprop-P, mefenacet, mefluidide, metam, metamitron, metazachlor, methabenzthiazuron, methazole, methoproptryne, methyldymron, methylisothiocyanate, metobromuron, fomosafen, fosamine, furyloxyfen, glufosinate, glyphosate, haloxyfop, hexazinone, imazamethabenz, imazapyr, imazaquin, imazethapyr, ioxynil, isopropalin, propyzamide, prosulfocab, pyrazolynate, pyrazolsulfuron, pyrazoxyfen, pyributicarb, pyridate, quinclorac, quinmerac, quinocloamine, quizalofop, quzizalofop-P, S-23121, sethoxydim, sifuron, simazine, simetryn, SMY 1500, sodium chlorate, sulfometuron, tar oils, TCA, metolachlor, metoxuron, metribzin, metsulfuron, molinate, monalide, monolinuron, MSMA, naproanilide, napropamide, naptalam, neburon, nicosulfuron, nipyraclofen, norflurazon, orbencarb, oaryzalin, oxadiazon, oxyfluorfen, paraquat, pebulate, pendimethalin, pentachlorophenol, pentaochlor, petroleum oils, phenmedipham, picloram, piperophos, pretilachlor, primisulfuron, prodiamine, proglinazine, propmeton, prometryn, propachlor, tebutam, tebuthiuron, terbacil, terbumeton, terbuthylazine, terbutryn, thiazafluoron, thifensulfuron, thiobencarb, thiocarbazil, tioclorim, tralkoxydim, tri-allate, triasulfuron, tribenzuron, trichlopyr, tridiphane, trietazine, trifluralin, IBI-C4874 vernolate, propanil, propaquizafop, propazine, propham.

The weight ratios of the active compounds in these active compound combinations can be varied within relatively large ranges.

The combinations of active compounds preferably obtain the active compound in an amount of from 0.1 to 99.9%, in particular from 1 to 75%, particularly preferably from 5 to 50%, the remainder up to 100% being made up by one or more of the above-mentioned co-components.

The microbicidal compositions or concentrates used for protecting industrial materials comprise the active compound or the active compound combination in a concentration of 0.01 and 95% by weight, in particular from 0.1 to 60% by weight.

The use concentration of the active compounds or the active compound combinations to be used depends on the kind and the occurrence of the microorganisms to be controlled and on the composition of the material to be protected. The optimum application rate can be determined by test series. The use concentrations are generally it in the range of from 0.001 to 5% by weight, preferably of from 0.05 to 1.0% by weight, based on the material to be protected.

The active compounds or compositions according to the invention allow, in an advantageous manner, the replacement of microbicidal compositions which are currently if available by more effective and less toxic compositions. They have good stability and, in an advantageous manner, a wide activity spectrum.

The examples below serve to illustrate the invention. The invention is not limited to the examples.

PREPARATION EXAMPLES

Example 2

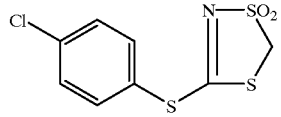

5 g (26 mmol) of 1,4,2-dithiazol-3-thiole 1,1-dioxide K-salt are dissolved in 13 ml of 20% strength KOH and mixed with 1.82 g of Cu powder and cooled to about 0° C. to 5° C. Within 30 minutes, the diazonium salt solution (I) is added dropwise and the reaction mixture is allowed to warm to room temperature and filtered off with suction. The filter cake is washed with water and subsequently taken up in ethyl acetate. The mixture is once more filtered and the filtrate is washed two times with 2 N HCl. The mixture is dried over $Na_2SO_4$, concentrated and chromatographed over silica gel (toluene/ethyl acetate=10:1).

To remove coloured impurities, the product is stirred with a little diisopropyl ether and filtered off with suction.

Yield: 2.9 g ($\Delta$ 39% of theory) of a slightly grey powder. mp.=172° C.

Diazonium Salt Solution (I):

At 2° C., 3.31 g (26 mmol) of 4-chloroaniline are initially charged in 46 ml of water and 6.5 ml of conc. HCl and admixed dropwise with a solution of 1.9 g of $NaNO_2$ in 15.6 ml of $H_2O$, and the mixture is stirred for 1 further hour.

Similar to this example and according to the general procedures above, the compounds of the formula (I) listed in Table 1 below are also prepared.

TABLE 1

(Dithiazole dioxides I)

| Example No. | Ar | R | Physical constants |
|---|---|---|---|
| 1 | phenyl | H | mp. = 124–125° C. |
| 2 | 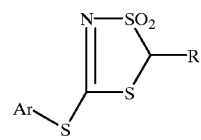 | H | mp. = 172° C. |

TABLE 1-continued
(Dithiazole dioxides I)
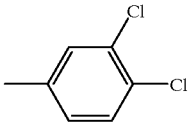
| Example No. | Ar | R | Physical constants |
|---|---|---|---|
| 3 | 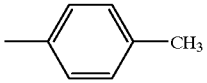 3,4-dichlorophenyl | H | mp. = 149° C. |
| 4 | 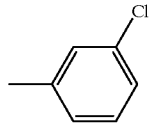 4-methylphenyl | H | mp. = 110° C. |
| 5 | 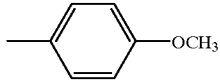 3-chlorophenyl | H | mp. = 154° C. |
| 6 | 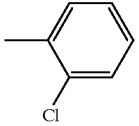 4-methoxyphenyl | H | mp. = 170° C. |
| 7 | 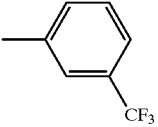 2-chlorophenyl | H | mp. = 137° C. |
| 8 | 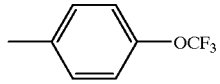 3-trifluoromethylphenyl | H | mp. = 138° C. |
| 9 | 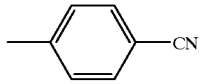 4-trifluoromethoxyphenyl | H | mp. = 138° C. |
| 10 | 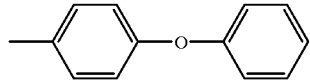 4-cyanophenyl | H | mp = 190° C. |
| 11 | 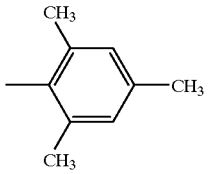 4-phenoxyphenyl | H | mp. = 127° C. |
| 12 | 2,4,5-trimethylphenyl | H | mp. = 227° C. |

TABLE 1-continued
(Dithiazole dioxides I)
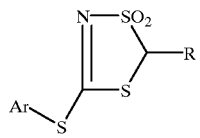
| Example No. | Ar | R | Physical constants |
|---|---|---|---|
| 13 | 4-F-C6H4 | H | mp. = 155° C. |
| 14 | 2,4-Cl2-C6H3 | H | mp. = 149° C. |
| 15 | 3-Cl-4-OCH3-C6H3 | H | mp. = 183° C. |
| 16 | 2,4-(CH3)2-C6H3 | H | mp. = 172° C. |
| 17 | 3,4-(OCH3)2-C6H3 | H | mp. = 169° C. |
| 18 | 4-C(CH3)3-C6H4 | H | mp. = 182° C. |
| 19 | C6H5 | —CH3 | |
| 20 | C6H5 | —C2H5 | |
| 21 | C6H5 | —CH2CH=CH2 | |
| 22 | 4-Cl-C6H4 | —CH3 | |

TABLE 1-continued (Dithiazole dioxides I)

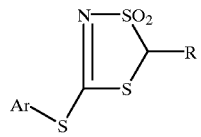

| Example No. | Ar | R | Physical constants |
|---|---|---|---|
| 23 |  | —CF₃ | |
| 24 |  | —CH₂—C≡CH | |
| 25 | 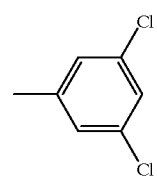 | H | mp. = 167° C. |

Use Example A

To assess the antifungal activity, the minimum inhibitory concentrations (MIC) of the compositions according to the invention are determined:

An agar which is prepared using malt extract is mixed with active compounds according to the invention at concentrations of from 0.1 mg/l to 5,000 mg/l. When the agar has set, it is contaminated with pure cultures of the test organisms listed in Table 2. The samples are stored for 2 weeks at 28° C. and 60 to 70% relative atmospheric humidity, after which the MIC is determined. The MIC is the lowest concentration of active compound at which no colonization by the microbe species used occurs, this concentration is listed in Table 2 below.

TABLE 2

Minimum inhibitory concentration (ppm) of compounds of the formula (I) according to the invention

| Example No. | 2 | 3 | 4 | Comparative Compound* |
|---|---|---|---|---|
| *Penicillium brevicaule* | <40 | <40 | <40 | 400 |
| *Chaetomium globosum* | <40 | <40 | <40 | 400 |
| *Aspergillus niger* | <40 | <40 | <40 | >400 |

*from U.S. Pat. No. 3,345,374, p. 2 Example No. 27

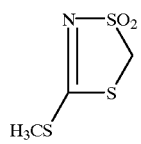

Example B

Phytophthora Test (tomato)/protective

Solvent: 4.7 parts by weight of acetone

Emulsifier: 0.3 parts by weight of alkyl-aryl polyglycol ether

To produce a suitable preparation of active compound, 1 part by weight of active compound is mixed with stated amounts of solvent and emulsifier, and the concentrate is diluted with water to the desired concentration.

To test for protective activity, young plants are sprayed with the active compound preparation until dew-moist. After the spray coating has dried on, the plants are inoculated with an aqueous spore suspension of Phytophthora infestans.

The plants are placed in an incubation cabin with 100% relative atmospheric humidity and about 20° C.

Evaluation is carried out 3 days after the inoculation.

At an active compound concentration of 100 ppm, the compound of Preparation Example 5 shows an efficacy of 90%. cl Example C Plasmopara Test (grapevines)/protective Solvent: 4.7 parts by weight of acetone Emulsifier: 0.3 parts by weight of alkyl-aryl polyglycol ether To produce a suitable preparation of active compound, one part by weight of active compound is mixed with the stated amounts of solvent and emulsifier, and the concentrate is diluted with water to the desired concentration.

To test for protective activity, young plants are sprayed with the active compound preparation until dew-moist. After the spray-coating has dried on, the plants are inoculated with an aqueous spore suspension of Plasmopara viticola and then remain in a humidity chamber at 20 to 22° C. and 100% relative atmospheric humidity for 1 day. The plants are subsequently placed in a greenhouse at 21 ° C. and about 90% atmospheric humidity for 5 days. The plants are then moistened and placed in a humidity chamber for 1 day.

Evaluation is carried out 6 days after the inoculation.

At an active compound concentration of 100 ppm, the compounds of Preparation Examples 1, 5 and 6 show an efficacy of more than 73%.

Example D
Botrytis Test (bean)/protective

Solvent: 4.7 parts by weight of acetone
Emulsifier: 0.3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation until dew-moist. After the spray coating has dried on, 2 small pieces of agar colonized with Botrytis cinerea are placed on each leaf. The inoculated plants are placed in a darkened moist chamber at 20° C. Three days after the inoculation, the size of the infected spots on the leaves is evaluated.

At an active compound concentration of 500 ppm, the compounds of Preparation Examples 1, 2, 5, 6 and 14 show an efficacy of more than 80%.

What is claimed is:

1. A compound of the formula (I)

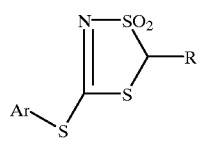

(I)

in which
R represents hydrogen, straight-chain or branched alkyl having 1 to 10 carbon atoms, straight-chain or branched alkenyl having 2 to 10 carbon atoms or straight-chain or branched alkinyl having 2 to 10 carbon atoms, which is optionally mono- to polysubstituted by identical or different substituents from the group consisting of halogen, alkoxy having 1 to 6 carbon atoms, halogenoalkoxy having 1 to 6 carbon atoms and 1 to 9 identical or different halogen atoms, alkylthio having 1 to 6 carbon atoms, halogenoalkylthio having 1 to 6 carbon atoms and 1 to 9 identical or different halogen atoms, acyl having 1 to 6 carbon atoms, acyloxy having 1 to 6 carbon atoms, (alkoxy)-carbonyl having 1 to 6 carbon atoms, amino, which is optionally substituted by identical or different substituents from the group consisting of alkyl and carbocyclic aryl of 6 to 10 carbon atoms, phenoxy, carbocyclic aryl of 6 to 10 carbon atoms, nitro or cyano, and Ar represents carbocyclic aryl of 6 to 10 carbon atoms, which is optionally mono- to pentasubstituted by halogen, alkyl having 1 to 10 carbon atoms, halogenoalkyl having 1 to 8 carbon atoms and 1 to 8 identical or different halogen atoms, alkoxy having 1 to 10 carbon atoms, halogenoalkoxy having 1 to 8 carbon atoms and 1 to 8 identical or different halogen atoms, alkylthio having 1 to 10 carbon atoms, halogenoalkylthio having 1 to 8 carbon atoms and 1 to 8 identical or different halogen atoms, amino, monoalkylamino having a straight-chain or branched alkyl radical having 1 to 6 carbon atoms, dialkylamino having identical or different, straight-chain or branched alkyl radicals having in each case 1 to 6 carbon atoms, cycloalkyl having 1 to 6 carbon atoms, methylenedioxy, difluoromethylenedioxy, chlorofluoromethylenedioxy, dichloromethylenedioxy, nitro or cyano.

2. A compound of the formula (I) according to claim 1 in which

R represents hydrogen, straight-chain or branched alkyl having 1 to 8 carbon atoms, straight-chain or branched alkenyl having 2 to 8 carbon atoms or straight-chain or branched alkinyl having 2 to 8 carbon atoms, which is optionally mono-totetrasubstituted by identical or different substitutents from the group consisting of fluorine, chlorine, alkoxy having 1 to 5 carbon atoms, halogenoalkoxy having 1 to 5 carbon atoms and 1 to 5 halogen atoms independently selected from the group consisting of fluorine and chlorine atoms, alkythio having 1 to 5 carbon atoms, halogenoalkylthio having 1 to 5 carbon atoms and 1 to 5 halogen atoms independently selected from the group consisting of fluorine and chlorine atoms, acyl having 1 to 5 carbon atoms, acyloxy having 1 to 5 carbon atoms, alkoxycarbonyl having 1 to 5 carbon atoms, amino which is optionally substituted by identical or different substituents from the group consisting of alkyl having 1 to 4 carbon atoms and phenyl, phenoxy, carbocyclic aryl of 6 to 10 carbon atoms, nitro or cyano, and Ar represents phenyl which is optionally mono- to tetra-subsfituted by fluorine, chlorine, alkyl having 1 to 8 carbon atoms, halogenoalkyl having 1 to 6 carbon atoms and 1 to 6 halogen atoms independently selected from the group consisting of fluorine and chlorine atoms, alkoxy having 1 to 8 carbon atoms, halogenoalkoxy having 1 to 6 carbon atoms and 1 to 6 halogen atoms independently selected from the group consisting of fluorine and chlorine atoms, alkylthio having 1 to 8 carbon atoms, halogenoalkylthio having 1 to 6 carbon atoms and 1 to 6 halogen atoms independently selected from the group consisting of fluorine and chlorine atoms, amino, monoalkylamino having an alkyl radical of 1 to 4 carbon atoms, dialkylamino having identical or different alkyl radicals having in each case 1 to 4 carbon atoms, cycloalkyl having 1 to 6 carbon atoms, methylenedioxy, difluoromethylenedioxy, chlorofluoromethylenedioxy, dichloromethylenedioxy, nitro or cyano.

3. A compound of the formula (I) according to claim 1 in which

R represents hydrogen, methyl, ethyl, n- or i-propyl, n-, s-, i- or t-butyl, allyl and propargyl which are optionally substituted by a substituent selected from the group consisting of fluorine, chlorine, methoxy and methylthio, and Ar represents phenyl which is optionally mono- to trisubstituted by substituents independently selected from the group consisting of chlorine, fluorine, methyl, ethyl, n- or i-propyl, n-, s-, i- or t-butyl, methoxy, ethoxy, trifluoromethyl, trifluoromethoxy, cyano and phenoxy.

4. A microbicidal composition comprising a microbicidally effective amount of a compound of the formula (I) according to claim 1 and an inert extender.

5. Method for controlling microorganisms comprising applying a microbicidally effective amount of a compound of the formula (I) according to claim 1 to the microorganisms, to their habitat or to an area where it is desirable to exclude microorganisms.

6. A process for preparing a compound of the formula (I) according to claim 1, comprising reacting a salt of the formula (II)

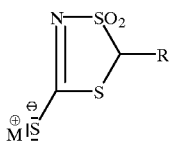

(II)

in which
  R is as defined in claim 2; and
  $M^\oplus$ represents an alkali metal or alkaline earth metal ion,
  with a diazonium salt of the formula (III)

$$Ar-N{=}N^\oplus A^\ominus \qquad (III)$$

in which
  Ar is as defined in claim 2; and
  $A^\ominus$ represents the anion of a mineral acid,
in an aqueous alkali metal hydroxide solution, between −30° C. and +60° C. optionally in the presence of a catalyst, which promotes the exchange of the diazonium function against sulfur-containing radicals.

7. Method for protecting industrial materials against microbial attack comprising applying to said industrial materials a microbicidally effective amount of a compound of the formula (I) according to claim 1.

8. The process of claim 6, wherein said alkali metal is selected from the group consisting of $Na^+$ and $K^+$.

* * * * *

UNITED STATES PATENT AND TRADEMARK OFFICE
CERTIFICATE OF CORRECTION

PATENT NO. : 6,197,799 B1  Page 1 of 1
DATED : March 6, 2001
INVENTOR(S) : Hermann Uhr et al.

It is certified that error appears in the above-identified patent and that said Letters Patent is hereby corrected as shown below:

<u>Title page,</u>
Item [56], References Cited, U.S. PATENT DOCUMENTS, add
-- 5,767,137  6/1998   Uhr et al. --

Signed and Sealed this

Ninth Day of September, 2003

JAMES E. ROGAN
*Director of the United States Patent and Trademark Office*